Sept. 18, 1973 R. G. JELLY Plant Pat. 3,402
WHITE ROSE PLANT
Filed Feb. 7, 1972
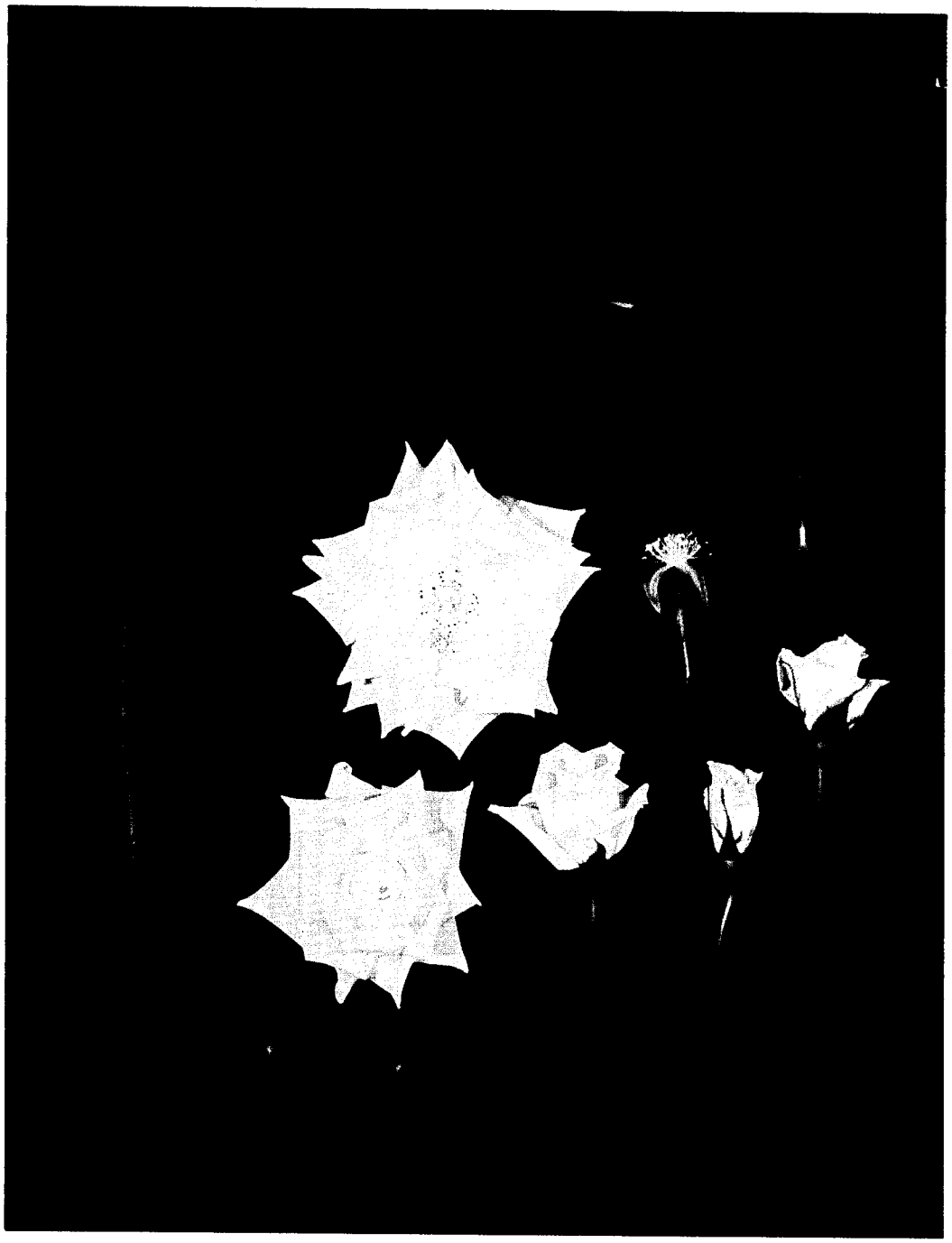

United States Patent Office

Plant Pat. 3,402
Patented Sept. 18, 1973

3,402

WHITE ROSE PLANT

Robert G. Jelly, Richmond, Ind., assignor to
E. G. Hill Co. Inc., Richmond, Va.

Filed Feb. 7, 1972, Ser. No. 224,349
Int. Cl. A01h *5/00*
U.S. Cl. Plt.—23 1 Claim

ABSTRACT OF THE DISCLOSURE

A new variety of rose plant bred for greenhouse production of cut flowers and distinguished by its abundant and continuous production of an almost pure white flower of excellent form, borne on medium to long moderately strong stems, and having a relatively long vase life at living room temperatures.

BACKGROUND OF THE INVENTION

The hereindescribed new variety of rose plant was developed by me at Richmond, Ind., with the object of producing an improved white flower having better form and color characteristics and a plant having a vigorous and free growth habit for the continuous production of the blooms to be marketed as cut flowers. This new plant originated as a seedling produced by crossing Jack Frost (P.P. 2,447) with Seventeen (P.P. 1,765) in January 1964 and with the blooming of the first flower in August 1964, it was evident that my objectives had been satisfactorily realized.

Asexual propagation of this new plant through succeeding generations by grafting at Richmond, Ind., and by budding at Livermore, Calif., has demonstrated that its distinguishing characteristics hold true from generation to generation and are firmly fixed.

DESCRIPTION OF THE DRAWING

My new variety of rose plant is illustrated by the accompanying drawing which shows the color characteristics of the new plant as nearly true as it is reasonably possible to obtain by conventional photographic procedures and which shows typical specimens of the bud in various stages of opening, a face view of the fully opened flower, specimens of typical leaves showing the venation of the leaflets, and specimens of young and mature wood.

DESCRIPTION OF THE NEW PLANT

The following is a detailed description of the new variety of rose plant as observed in greenhouse at Richmond, Ind., with color designations according to the R.H.S. Colour Chart of The Royal Horticultural Society, Nickerson's "Color Fan," and Wilson's "Hortcultural Colour Chart" as published by The Royal Horticultural Society, identified herein as (R), (N), and (W), respectively.

*The plant*

Origin: Seedling (#8–65WS).
Parentage:
*Seed parent.*—Jack Frost (P.P. 2,447).
*Pollen parent.*—Seventeen (P.P. 1,765).
Classification: Hybrid tea—Polyantha.
Type: Greenhouse seedling for cut flower production.
Form: Bush.
Growth: Free, vigorous, upright and much branched, with canes of medium diameter.
Main stems: Color—Yellow Green 147B (R).
*Thorns.*—Several, of medium length, and hooked downward from a moderately short and narrow base.
*Color.*—Greyed-Orange 165B (R) at the base to slightly darker than 165B (R) at the tip.
*Prickles and Hairs.*—None.

Branches:
*Thorns.*—Few to several, long to medium in length and slightly hooked downward from a moderately short and narrow base.
*Color of thorns.*—Lighter than Red 53B (R) to almost translucent.
*Prickles.*—None.
Foliage: Quantity—moderately abundant.
*Shape.*—Compound and odd pinnate.
*Size.*—Moderately small.
*Leaflets.*—Number—3 to 5, mostly 7. Shape.—Elliptical with cuspidate apex, oblique base, and serrate margin. Texture—Thick leathery. Color—Mature, upper side—Yellow Green 147A (R). Mature, under side—Yellow Green 147C (R). Young, upper side—Yellow Green 146A (R) suffused with venation variation of Red 53C (R). Young, under side—Willow Green 000862/1 (W) suffused with venation variation of Red 50B (R).
*Rachis.*—Light to medium. Upper side—grooved and prickly. Under side—prickly to thorny.
*Stipules.*—Medium in length and width, with points which are medium to moderately long, turning outward somewhat less than 90°.

*The bud*

Size: Medium small.
Form: Before calyx breaks—short pointed to globular without conspicuous neck. Foliaceous appendages on bud surface with parts extending beyond the tip a distance equal to ¼ or more of the bud length. Color: Shaded from Pod Green 061 (W) at base to Yellow Green 146B (R) to a slight shade of red at the top of the foliaceous appendage. As calyx breaks, the form and outside color remain the same.
Color: As first petal opens—color of petals. Outside: White 155B (R) to Yellow Green 150C (R) to 150D (R) at the base. Inside: White 155A (R) to Yellow Green 150C (R) to Yellow Green 150D (R) at the base.
Sepals: Spear shaped. Curl back as flower opens. Color: Shaded from Pod Green 061 (W) at base to Yellow-Green 146B (R).
Peduncle: Size—medium length and diameter.
*Strength.*—Strong and erect.
*Bark.*—Smooth with prickles. Color: Yellow Green 146B (R).
*Prickles.*—Few to numerous. Color: Red 36C (R) to almost translucent.
*Hairs.*—None.
Opening character: Bud opens well in greenhouse. It is affected by hot weather by decrease of bud size.

*The flower*

Blooming habit: Continuous, free and abundant.
Size: When fully opened—Medium, 2½ to 3½ inches in diameter.
Form: High centered at first with petals rolled outward becoming flat to globular with petals remaining rolled outward.
Borne: One to occasionally two or three to a stem, pyramidal in cluster on medium strong, medium long stems. Multiple flowers are disbudded to one.
Petalage: Double—from 27 to 32 petals arranged regularly.
*Shape.*—Outside—oval, with one to several notches in apex. Intermediate—oval, apex with 2 to 3 notches. Inside—oval to scalloped, apex occasionally has one notch.
*Color.*—May be modified by being shaded with other colors.

The following is the color description, made in April 1971, of a newly opened flower taken from a greenhouse rose grown at Richmond, Ind.:

*Outside petal.*—Outer and inner surfaces—shaded from Yellow-Green 145C (R) at the base to White 155B (R).

*Intermediate petal.*—Same as outside petal.

*Inner petal.*—Outer and inner surfaces—shaded from Yellow-Green 145C (R) at the base to Green-White 157D (R).

The following color description is from a greenhouse rose grown at Richmond, Indiana, and opened for three days in April 1971:

*Outside, intermediate and inner petals.*—Outer surfaces—shaded from Yellow-Green 145C (R) at the base to White 155B (R). Inner surfaces—shaded from Yellow-Green 145C (R) at the base to White 155B (R).

General color effect: The newly opened flower is mainly an overall White 155D (R) with a very light Aureolin 3/3 (W) cast at the center of the blossom. As the blossom matures, the color appears to darken slightly, as in a three days opened flower which has a general coloring slightly lighter than White 155A (R).

*Texture.*—Leathery and moderately thick.

*Appearance.*—Velvety, inside and outside.

*Fragrance.*—Moderate sweetbriar.

*Persistence.*—Petals hang on and dry.

*Effect of weather.*—Not material. Outside petals brown with age.

*Lasting quality.*—As a cut flower—7 to 8 days at living room temperatures.

*Reproductive organs*

Stamens: Of medium number, arranged irregularly about the pistils.

*Anthers.*—Medium small to large, all open at once.

Color: Shaded from Yellow Orange 21B (R) to 21C (R).

*Filaments.*—Short to medium in length, mostly with anthers. Color: Shaded from Yellow-Green 145D (R) to 149D (R).

*Pollen.*—Abundant. Color: Shaded from Yellow-Orange 21C (R) to 21B (R).

Pistils: Of medium number.

*Styles.*—Uneven, medium to long in length, moderately thin and bunched. Color: From Yellow-Green 150D to 149D (R).

*Stigma color.*—Shaded from Yellow-Green 154B to 150D (R).

*Ovaries.*—All encased in calyx.

*Hips.*—None available.

My new variety of rose plant is an improvement over the seed parent, Jack Frost (P.P. 2,447), in that it has a more pointed and attractive bud, a longer stem and its blossoms are of a whiter color. The new plant is also a material improvement over its pollen parent, Seventeen (P.P. 1,765), because it has a more vigorous growth, its blossoms have a better and more pleasing texture and, as a cut flower, it has a longer lasting vase life under ordinary living room temperatures. The combination of these advantageous factors provides a new and improved rose plant of real commercial value as a strong producer of an almost pure white flower particularly suitable for the cut flower market.

I claim:

1. A new and distinct variety of rose plant substantially as herein shown and described, characterized by the very white color of its blossoms, its continuous and abundant production of flowers on strong stems of medium length, and its vigorous growth under greenhouse culture.

No references cited.

ROBERT E. BAGWILL, Primary Examiner